US012702646B2

(12) United States Patent
Minrovic et al.

(10) Patent No.: US 12,702,646 B2
(45) Date of Patent: Aug. 11, 2026

(54) MICROSPHERE FORMULATIONS COMPRISING NALMEFENE AND METHODS FOR MAKING AND USING THE SAME

(71) Applicants: OAKWOOD LABORATORIES, LLC., Oakwood Village, OH (US); EMERGENT PRODUCT DEVELOPMENT GAITHERSBURG INC., Gaithersburg, MD (US)

(72) Inventors: Bradley Minrovic, Stow, OH (US); Regan Cote, Lakewood, OH (US); Michael Whelehan, Dublin (IE); Andrew Walker, Belfast (GB); Parissa Heshmati, Oakland, CA (US); Brenda Hunter Perkins, Birmingham, AL (US); Gary Anthony Winchester, Warrior, AL (US); Yiming Ma, Vestavia Hills, AL (US)

(73) Assignees: OAKWOOD LABORATORIES, LLC., Oakwood Village, OH (US); EMERGENT PRODUCT DEVELOPMENT GAITHERSBURG INC., Gaithersburg, MD (US)

( * ) Notice: Subject to any disclaimer, the term of this patent is extended or adjusted under 35 U.S.C. 154(b) by 217 days.

(21) Appl. No.: 18/554,744

(22) PCT Filed: Apr. 20, 2022

(86) PCT No.: PCT/US2022/071813

§ 371 (c)(1),
(2) Date: Oct. 10, 2023

(87) PCT Pub. No.: WO2022/226505

PCT Pub. Date: Oct. 27, 2022

(65) Prior Publication Data

US 2024/0216280 A1 Jul. 4, 2024

Related U.S. Application Data

(60) Provisional application No. 63/177,015, filed on Apr. 20, 2021.

(51) Int. Cl.
*A61K 9/16* (2006.01)
*A61K 31/485* (2006.01)

(52) U.S. Cl.
CPC .......... *A61K 9/1647* (2013.01); *A61K 9/1694* (2013.01); *A61K 31/485* (2013.01)

(58) Field of Classification Search
CPC ... A61K 9/1647; A61K 9/1694; A61K 9/0019
See application file for complete search history.

(56) References Cited

U.S. PATENT DOCUMENTS 6,103,258 A 8/2000 Simon
7,157,102 B1 1/2007 Nuwayser
(Continued)

FOREIGN PATENT DOCUMENTS

WO 2022198167 A1 9/2022

OTHER PUBLICATIONS

International Search Report issued Aug. 30, 2022 in Intl. Appl. No. PCT/US22/71813.

*Primary Examiner* — Carlos A Azpuru
(74) *Attorney, Agent, or Firm* — MEDLER FERRO WOODHOUSE & MILLS PLLC

(57) ABSTRACT

Microsphere formulations comprising nalmefene are provided. In one aspect, the microsphere formulations are characterized in that the nalmefene is released over a period of about 60 days or more. Methods for making and using the microsphere formulations are also provided.

32 Claims, 4 Drawing Sheets

(56) References Cited

U.S. PATENT DOCUMENTS

| | | | | |
|---|---|---|---|---|
| 2004/0018238 | A1 | 1/2004 | Shukla | |
| 2005/0031668 | A1 | 2/2005 | Patel | |
| 2016/0136096 | A1* | 5/2016 | Markland | A61L 31/10<br>424/501 |

* cited by examiner

MICROSPHERE FORMULATIONS COMPRISING NALMEFENE AND METHODS FOR MAKING AND USING THE SAME

CROSS-REFERENCE TO RELATED APPLICATIONS

This application claims priority from U.S. Provisional Patent Application No. 63/177,015, filed on Apr. 20, 2021, which is incorporated by reference herein in its entirety.

BACKGROUND

Nalmefene (chemical formula $C_{21}H_{25}NO_3$; CAS Number 55096-26-9), characterized by the general structure:

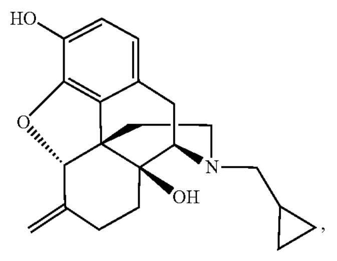 [SMILES: C=C1CC[C@@]2(O)[C@H]3Cc4ccc(O)c5c4[C@@]2(CCN3CC2CC2)[C@H]1O5]

is a medication used to treat alcohol and opioid dependence.

In the United States, immediate-release injectable nalmefene was approved in 1995 as an antidote for opioid overdose. It was sold under the brand name REVEX®.

Nalmefene is an opiate derivative similar in both structure and activity to the opioid antagonist naltrexone. Naltrexone is currently available and in development as an extended-release microsphere formulation (commercially available under the trade name Vivitrol®; chemically distinct naltrexone-containing polymer microsphere formulations are disclosed in International Patent Application No. PCT/US2022/070941).

Advantages of nalmefene relative to naltrexone include longer half-life, greater oral bioavailability, and no observed dose-dependent liver toxicity. Thus, a need exists for an extended-release nalmefene-encapsulating microsphere formulation.

SUMMARY

Microsphere formulations comprising nalmefene are provided. In one aspect, the microsphere formulations comprise polymer microspheres (sometimes referred to herein as "microparticles"), each polymer microsphere comprising: (i) nalmefene; and (ii) a biodegradable polymer, wherein each polymer microsphere comprises a drug load of nalmefene of at least about 40% by weight of the polymer microsphere, and wherein the polymer microspheres have an average particle size of about 10 μm to about 40 μm ($D_{50}$). In one aspect, the microsphere formulations are characterized in that the nalmefene is released over a period of about 60 days. In another aspect, the microsphere formulations are characterized in that they have a low initial burst release, that is, not more than 50% of the nalmefene is released within about four hours of injection into a subject.

In one aspect, the microsphere formulations may be made by a method, the method comprising: (A) mixing: (i) the biodegradable polymer; (ii) a primary solvent; (iii) nalmefene; and (iv) a co-solvent, to form a dispersed phase; (B) mixing: (i) water; and (ii) a surfactant, to form a continuous phase; and (C) combining the dispersed phase with the continuous phase in a homogenizer.

In one aspect, a method for treating alcohol and/or opioid dependence is provided. The method may comprise administering by intramuscular or subcutaneous injection to a patient in need thereof a microsphere formulation made according to the methods described herein, wherein the formulation is administered to the patient with a dosing schedule of about every 60 days.

In another aspect, use is disclosed of a microsphere formulation comprising polymer microspheres, each polymer microsphere comprising: (i) nalmefene; and (ii) a biodegradable polymer, wherein each polymer microsphere comprises a drug load of nalmefene of at least 40% by weight of the polymer microsphere, and wherein the polymer microspheres have an average particle size of about 10 μm to about 40 μm ($D_{50}$), in the manufacture of a medicament for the treatment of alcohol and/or opioid dependence.

In another aspect, a microsphere formulation comprising polymer microspheres, each polymer microsphere comprising: (i) nalmefene; and (ii) a biodegradable polymer, wherein each polymer microsphere comprises a drug load of nalmefene of at least 40% by weight of the polymer microsphere, and wherein the polymer microspheres have an average particle size of about 10 μm to about 40 μm ($D_{50}$), is provided for use as a medicament for the treatment of alcohol and/or opioid dependence.

In another aspect, a kit is provided, the kit comprising polymer microspheres, each polymer microsphere comprising: (i) nalmefene; and (ii) a biodegradable polymer, wherein each polymer microsphere comprises a drug load of nalmefene of at least 40% by weight of the polymer microsphere, and wherein the polymer microspheres have an average particle size of about 10 μm to about 40 μm ($D_{50}$). In some aspects, the kit further comprises a diluent for administration of the polymer microspheres to a patient.

DETAILED DESCRIPTION

Figure 1:
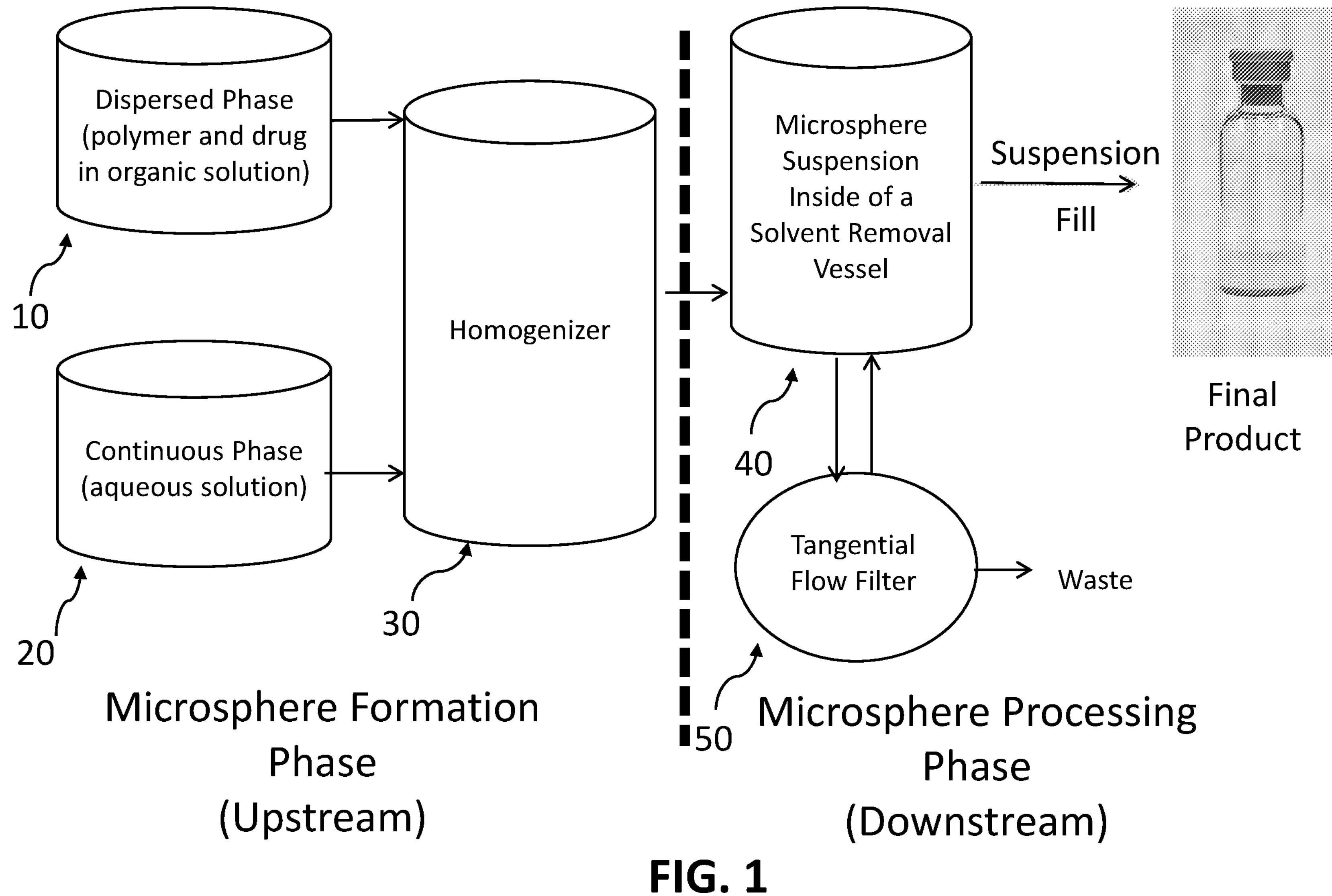
FIG. 1 is a schematic depicting a method for making nalmefene-encapsulated polymer microspheres.

Microsphere formulations comprising nalmefene are provided. In one aspect, the microsphere formulations comprise polymer microspheres, each polymer microsphere comprising: (i) nalmefene; and (ii) a biodegradable polymer, wherein each polymer microsphere comprises a drug load of nalmefene of at least about 40% by weight of the polymer microsphere, and wherein the polymer microspheres have an average particle size of about 10 μm to about 40 μm ($D_{50}$). In one aspect, the microsphere formulations are characterized in that the nalmefene is released over a period of about 60 days. In another aspect, the microsphere formulations are characterized in that they have a low initial burst release, that is, not more than 20% of the nalmefene is released within about 24 hours of injection into a subject.

In one aspect, the microsphere formulations may be made by a method, the method comprising: (A) mixing: (i) the biodegradable polymer; (ii) a primary solvent; (iii) nalmefene; and (iv) a co-solvent, to form a dispersed phase; (B) mixing: (i) water; and (ii) a surfactant, to form a continuous phase; and (C) combining the dispersed phase with the continuous phase in a homogenizer.

Nalmefene

In one aspect, the nalmefene is a free base supplied by Mallinckrodt Pharmaceuticals, having a molecular weight of 339 dL/g, a purity of 99.5%, and water solubility of 0 mg/mL. In another aspect, the nalmefene is supplied as a pharmaceutically acceptable salt.

Biodegradable Polymers

In one aspect, the biodegradable polymer is a poly (D,L-lactide-co-glycolide) polymer (a "PLGA"). A PLGA is a biodegradable polyester which degrades in the human body by random chain hydrolysis into its non-toxic monomeric components, i.e., lactic acid and glycolic acid. PLGA is a general term used to describe a group of polymers. In general, these polymers are either synthesized by ring opening polymerization of the respective lactic acid dimers (lactide rings) and glycolic acid dimers (glycolide rings) or by polycondensation of lactic acid and glycolic acid monomers. Polymerization is typically initiated by either water or by an alkyl alcohol, such as dodecanol, to yield a PLGA that is either acid or ester end-capped, respectively.

The lactide:glycolide or "l:g" ratio may be tailored to provide the desired release characteristics of the microparticles. Tailoring of the desired l:g ratio may be carried out by selecting the starting amounts of lactide and glycolide during the PLGA production process and applying the desired polymerization process to result in the desired l:g ratio of the end, microsphere product. In one aspect, the monomer ratio is between about 80:20 and about 90:10, including about 80:20, about 85:15, or about 90:10. In some aspects, the l:g ratio may be between 81:19 to 89:11, or between 82:18 to 88:12, between 83:17 to 87:13, between 84:16 to 86:14, or about 85:15. Suitably the l:g ratio is 85:15, as described herein.

The molecular weight of the PLGA may also be selected to impart the desired release characteristics. The molecular weight of the PLGA may be between about 40-90 kDa, between about 50-80 kDa, between about 50-70 kDa, between about 50-60 kDa, between about 60-80 kDa, between about 70-80 kDa, or about 50 kDa, about 60 kDa, about 70 kDa, about 80 kDa, or about 90 kDa.

The polymer end-caps of the PLGA that make up the microspheres suitably are acid end-caps, though in other embodiments, ester end-caps can be utilized.

In some aspects, the biodegradable polymer may have an inherent viscosity of about 0.6 dL/g to about 0.8 dL/g.

Thus, in one aspect, the polymer comprises an 85:15, acid terminated PLGA having IV=0.62 dL/g and MW=78.4 kDa.

Dispersed Phase

In one aspect, the dispersed phase comprises a primary solvent. In one aspect, the primary solvent comprises ethyl acetate (EA). The dispersed phase may also include up to about 50% by weight (or up to about 30% by weight, up to about 35% by weight, up to about 40% by weight, up to about 45% by weight, up to about 55% by weight, or up to about 60% by weight) of a co-solvent capable of optimizing the solubility of the nalmefene. In one aspect, the co-solvent may be dimethyl sulfoxide (DMSO), benzyl alcohol (BA), dichloromethane (DCM), dimethyl formamide (DMF), dimethyl acetamide (DMAc), acetonitrile (ACN), ethanol (EtOH), N-methyl pyrrolidone (NMP), or any other solvent that increases the solubility of nalmefene in the dispersed phase containing EA. In one aspect, the primary solvent comprises EA, and the co-solvent comprises DMSO. In one aspect, the ratio of EA to DMSO is about 2:1. The organic solvent is removed from the microspheres in the course of their preparation. A microsphere is considered to be "essentially free" of organic solvent if the microsphere meets the standards set forth in the "ICH Harmonised Guideline, Impurities: Guideline for Residual Solvents Q3C(R8), Current Step 4 version dated 22 Apr. 2021," which is incorporated herein by reference in its entirety.

Continuous Phase

The dispersed phase may be combined with an aqueous continuous phase that comprises water and, optionally, a surfactant. In one aspect, the continuous phase is unbuffered.

The surfactant component may be present in the continuous phase in an amount of about 0.35% to about 1.0% by weight in water. In one aspect, the surfactant component comprises polyvinyl alcohol (PVA) in a concentration of 0.35% by weight in water, or about 0.20% by weight in water, about 0.25% by weight in water, about 0.30% by weight in water, about 0.40% by weight in water, or about 0.45% by weight in water.

In some aspects, the dispersed phase flow rate to the homogenizer may be from about 50 mL/min to about 200 mL/min, including about 75 mL/min to about 180 mL/min, about 100 mL/min to about 180 mL/min, about 100 mL/min to about 150 mL/min, about 100 mL/min, and about 180 mL/min. In some aspects, the continuous phase flow rate to the homogenizer may be about 0.25 L/min to 0.75 mL/min, including about 0.5 L/min to about 0.70 mL/min, about 0.5 L/min to about 0.6 L/min, about 0.5 L/min, or about 0.54 L/min. In one aspect, the continuous phase:dispersed phase ratio may be from about 10:1 to about 1:1, including about 7:1 to about 4:1, about 6:1 to about 3:1, about 5:1, and about 3:1.

The continuous phase may be provided at room temperature or above or below room temperature. In some aspects, the continuous phase may be provided at about 40° C., about 37° C., about 35° C., about 30° C., about 25° C., about 20° C., about 15° C., about 10° C., about 5° C., about 0° C., and any range or value between any of those values.

Homogenizer

For brevity, and because the methods are equally applicable to either, the phrase "homogenizer" contemplates a system or apparatus that can homogenize the dispersed phase and the continuous phase, emulsify the dispersed phase and the continuous phase, or both, which systems and apparatuses are known in the art. For example, in one aspect, the homogenizer is an in-line Silverson Homogenizer (commercially available from Silverson Machines, Waterside UK) or a Levitronix® BPS-i100 integrated pump system used, e.g., as described in U.S. Pat. No. 11,167,256, which is incorporated by reference herein in its entirety. In one aspect, the homogenizer is a membrane emulsifier. In one aspect, the homogenizer runs at an impeller speed of about 1,000 to about 4,000 revolutions per minute ("RPM"), including about 1,500 RPM, about 2,000 RPM, and about 2,500 RPM.

Drug Load

In some aspects, the nalmefene base is loaded into the microparticle at an amount of at least 20 w/w %, relative to the microparticle. That is, the amount (weight amount) of nalmefene loaded into the microparticle is at least 20% of the weight of the total microparticle, and thus is expressed as a weight/weight (w/w) percentage. In some aspects, the nalmefene may be loaded into the microparticle in an amount of at least 21 w/w %, at least 22 w/w %, at least 23 w/w %, at least 24 w/w %, at least 25 w/w %, at least 26 w/w %, at least 27 w/w %, at least 28 w/w %, at least 29 w/w %, at least 30 w/w %, at least 31 w/w %, at least 32 w/w %, at least 33 w/w %, at least 34 w/w %, at least 35 w/w %, at least 36 w/w %, at least 37 w/w %, at least 38 w/w %, at least 39 w/w %, at least 40 w/w %, or between 20-40 w/w %, between 20-35 w/w %, between 25-35 w/w %, or between 20-30 w/w %.

In some aspects, the drug load of each polymer microsphere may be greater than 25 wt/wt %, greater than 30 wt/wt %, about 40 wt/wt %, greater than about 40 wt/wt %, greater than about 50 wt/wt %, greater than about 60 wt/wt %, or greater than about 70 wt/wt %. In some aspects, each polymer microsphere has a nalmefene drug load of about 35 wt/wt % to about 50 wt/wt %, including about 40 wt/wt % to about 45 wt/wt %.

Average Particle Size

As used herein, "average particle size" refers to the size of a polymer microsphere measured using one or more particle size measurements (e.g., dynamic light scattering or scanning electron microscopy (SEM)) and is a weighted mean size. Typically, the average particle size will be indicative of the diameter of a spherical microparticle.

In some aspects, the microparticles containing nalmefene and comprising PLGA described herein have an average particle size ($D_{50}$) of between about 10 μm to about 120 μm, about 10 μm to about 100 μm, about 60 μm to about 90 μm, about 60 μm to about 80 μm, about 70 μm to about 80 μm, about 70 μm to about 75 μm, about 75 μm to about 80 μm, or about 70 μm, about 71 μm, about 72 μm, about 73 μm, about 74 μm, about 75 μm, about 76 μm, about 77 μm, about 78 μm, about 79 μm, or about 80 μm.

In one aspect, the polymer microspheres may have an average particle size between about 10 μm ($D_{50}$) and about 40 μm ($D_{50}$), including about 15 μm ($D_{50}$), about 20 μm ($D_{50}$), about 25 μm ($D_{50}$), about 30 μm ($D_{50}$), and about 35 μm ($D_{50}$). In some aspects, the polymer microspheres may have an average particle size of between about 10 μm and about 30 μm ($D_{50}$), including between about 15 μm and about 25 μm ($D_{50}$).

Extended Release

As described herein, the nalmefene formulations are designed to release a therapeutically effective amount of nalmefene to a patient, following injection, over a sustained period. In one aspect, the formulations release nalmefene at an amount of at least 0.5 ng/ml over a sustained period of at least 60 days, 70 days, or 80 days.

As used herein a "sustained period" or a "sustained release" or a "duration of release" means the average amount of nalmefene released over the stated period is at or above the amount desired for treatment. That is, release of nalmefene of at least 0.5 ng/mL over a sustained period of at least 80 days, means that for each of the days following injection, the average amount of nalmefene released into the patient is at or above about 0.5 ng/mL for the entire 80 day period. In some aspects, the formulations described herein release at least 0.6 ng/ml of nalmefene over a sustained period of at least 80 days, or in some aspects, the amount released is at least 0.7 ng/ml, at least 0.8 ng/ml, at least 0.9 ng/ml, at least 1.0 ng/mL, at least 1.1 ng/ml, at least 1.2 ng/ml, at least 1.3 ng/ml, at least 1.4 ng/mL, at least 1.5 ng/mL, or between 1.0 ng/mL-1.5 ng/ml, between 1.0 ng/ml-1.4 ng/mL, between 1.0 ng/ml-1.3 ng/mL, between 1.1 ng/mL-1.4 ng/mL, between 1.2 ng/ml-1.4 ng/ml, or about 1.3 ng/mL, over a sustained period of at least 60, 70, or 80 days.

In further aspects, the amount of nalmefene released is released over a sustained period of at least 81 days, at least 82 days, at least 83 days, at least 84 days, at least 85 days, at least 86 days, at least 87 days, at least 88 days, at least 89 days, at least 90 days, at least 91 days, at least 92 days, at least 93 days, at least 94 days, at least 95 days, at least 96 days, at least 97 days, at least 98 days, at least 99 days, at least 100 days, or over a sustained period of 80 days to 100 days, a period of 85 days to 95 days, a period of 87 days to 93 days, a period of 88 days to 92 days, a period of 80 to 90 days, or a period of 90 days to 100 days.

In one aspect, the microsphere formulations are characterized in that they have a duration of release of about 60 days, or about 40 days, about 50 days, about 70 days, or about 80 days. In one aspect, the microsphere formulations are characterized in that they have a duration of release of more than 60 days, including in that about 75% to just less than 100% of the nalmefene is released within about 60 days of injection. In another aspect, the microsphere formulations are characterized in that they have a low initial burst release, that is, not more than about 20% of the nalmefene is released within about 24 hours of injection into a subject, including not more than about 10% to about 30%, not more than about 20% to about 40%, not more than about 30% to about 50%, not more than about 30%, not more than about 35%, or not more than about 40% of the nalmefene is released within about 24 hours of injection into a subject.

The microparticle formulations described herein can be formulated in various excipient and buffer mixtures and can also include ingredients to provide the desired osmolarity to match or closely approach that of the body. Additional excipients include various sugars, salts, suspending agents, antibacterial agents, preservatives etc. Examples of excipients include, but are not limited to, water, one or more antibacterials (e.g., amphotericin B, chloretracycline, gentamicin, neomycin), one or more preservatives (e.g., benzethonium chloride, EDTA, formaldehyde, 2-phenoxyethanol), one or more buffers (e.g., phosphate buffers, sodium borate, sodium chloride), one or more surfactants (polysorbate 20, 80), one or more protein stabilizers (e.g., albumin, lactose, potassium glutamate), sugars e.g. sucrose or dextrose, and adjuvants (e.g., aluminum hydroxide, aluminum phosphate). In some aspects, the microparticle formulations include the following excipients: water, carboxymethylcellulose sodium, polysorbate 20, and sodium chloride. The nalmefene formulation can be stored as a solution for injection (suitably refrigerated) or can be freeze-dried, lyophilized, dried, or otherwise prepared in a manner that can later be reconstituted (using, e.g., sterile water or a composition including water, carboxymethylcellulose sodium, polysorbate 20, and sodium chloride) prior to injection into a patient.

Therapeutic Benefits

In one aspect, a method for treating alcohol and/or opioid dependence is provided. The method may comprise administering by intramuscular or subcutaneous injection to a patient in need thereof a microsphere formulation made according to the methods described herein, wherein the formulation is administered to the patient with a dosing schedule of about every 60 days, or about every 40 days, about every 50 days, about every 70 days, or about every 80 days.

In another aspect, use is disclosed of a microsphere formulation comprising polymer microspheres, each polymer microsphere comprising: (i) nalmefene; and (ii) a biodegradable polymer, wherein each polymer microsphere comprises a drug load of nalmefene of at least 40% by weight of the polymer microsphere, and wherein the polymer microspheres have an average particle size of about 10 μm to about 40 μm ($D_{50}$), in the manufacture of a medicament for the treatment of alcohol and/or opioid dependence.

In another aspect, a microsphere formulation comprising polymer microspheres, each polymer microsphere comprising: (i) nalmefene; and (ii) a biodegradable polymer, wherein each polymer microsphere comprises a drug load of nalmefene of at least 40% by weight of the polymer microsphere, and wherein the polymer microspheres have an average particle size of about 10 μm to about 40 μm ($D_{50}$), is provided for use as a medicament for the treatment of alcohol and/or opioid dependence.

In another aspect, a kit is provided, the kit comprising polymer microspheres, each polymer microsphere comprising: (i) nalmefene; and (ii) a biodegradable polymer, wherein each polymer microsphere comprises a drug load of nalmefene of at least 40% by weight of the polymer microsphere, and wherein the polymer microspheres have an average particle size of about 10 μm to about 40 μm ($D_{50}$). In some aspects, the kit further comprises a diluent for administration of the polymer microspheres to a patient.

Examples of substance use disorders that can be treated using the methods and formulations described herein include, but are not limited to, alcohol use disorder, cannabis use disorder, methamphetamine use disorder, cocaine use disorder, nicotine use disorder, opioid use disorder, and hallucinogen use disorder. In one aspect, the substance use disorder that is treated using the methods described herein is opioid use disorder, which includes the abuse/use of opioids such as OXYCOTIN®, VICODIN®, and fentanyl.

In some aspects, the microparticle formulation is lyophilized or otherwise stored in a dried form, or a lyophilized form, prior to being administered to the patient. Prior to administration, the dried form is reconstituted by adding a diluent, for example, sterile water, or a composition comprising water, carboxymethylcellulose sodium, polysorbate 20, and sodium chloride, to the lyophilized form of the formulation prior to the administering.

Various routes of administration may be used, including intravenous injection, subcutaneous injection, peritoneal injection, and intramuscular injection.

EXAMPLES

Example 1—General Preparation of Polymer Microspheres Comprising Nalmefene Via a Single Emulsion Method Microsphere Formation Phase. With reference to FIG. 1, a dispersed phase ("DP") 10 is formed by dissolving a polymer matrix (such as a PGLA polymer) in an organic solvent system (such as EA and DMSO), followed by the addition of nalmefene with mixing until completely dissolved. The DP 10 is filtered using a 0.2 μm sterilizing PTFE or PVDF membrane filter (such as EMFLON, commercially available from Pall or SartoriousAG) and pumped into a homogenizer 30, such as an in-line Silverson Homogenizer (commercially available from Silverson Machines, Waterside UK) or a Levitronix i100 (as described in U.S. Pat. No. 11,167,256), at a defined flow rate. A continuous phase ("CP") 20 comprising water and surfactant is also pumped into the homogenizer 30 at a defined flow rate. The speed of the homogenizer 30 is generally fixed to achieve a desired polymer microsphere size distribution. A representative continuous "upstream" microsphere formation phase is described in U.S. Pat. No. 5,945,126, which is incorporated by reference herein in its entirety.

Microsphere Processing Phase. The formed or forming microspheres exit the homogenizer 30 and ultimately enter a solvent removal vessel ("SRV") 40. Water may be added to minimize the solvent level in the aqueous medium. See, e.g., U.S. Pat. No. 9,017,715, which is incorporated by reference herein in its entirety. After the DP 10 has been exhausted, the CP 20 and water flow rates are stopped, and the washing steps are initiated. Solvent removal is achieved using water washing and a hollow fiber filter (commercially available as HFF from GE Healthcare) 50. A representative "downstream" microsphere processing phase is described in U.S. Pat. No. 6,270,802, which is incorporated by reference herein in its entirety.

The washed microspheres are collected and freeze-dried overnight in a lyophilizer (Virtis) to remove any moisture. The resulting microspheres are a free-flowing off-white bulk powder.

Example 2—Preparation of PLGA-Based Nalmefene-Encapsulated Polymer Microspheres Batch 1: Following the general procedure described in Example 1 and illustrated in FIG. 1, the DP was formed by dissolving 5.5 g of 85:15, acid terminated PLGA having IV=0.62 dL/g and MW=78.4 kDa in 49.75 g of EA and 9.0 g of DMSO (EA:DMSO (5.5:1)), followed by addition of nalmefene (4.5 g) with mixing until completely dissolved. The DP was filtered and pumped at a flow rate of 250 mL/min into a Levitronix® BPS-i100 integrated pump system operating at 2,500 RPM. The CP comprising 0.35% PVA was also pumped into the homogenizer at a flow rate of 0.25 L/min (CP:DP=1:1).

The formed or forming microspheres exited the homogenizer and entered the SRV. Room temperature deionized water was added to the SRV, followed by water washing (room temperature and 35-39° C.) and a hollow fiber filter.

The bulk suspension was collected via filtration and lyophilized to obtain a free-flowing powder with a yield of about 65%. The drug load was 42.4 wt/wt % (94% drug encapsulation efficiency based on a target drug load of 45 wt/wt %). The average particle size was 10 μm ($D_{10}$), 19 μm ($D_{50}$), 31 μm ($D_{90}$). Residual solvents were EA=0.1% and DMSO=1.3%. The sample molecular weight was 75 kDa.

Figure 2:
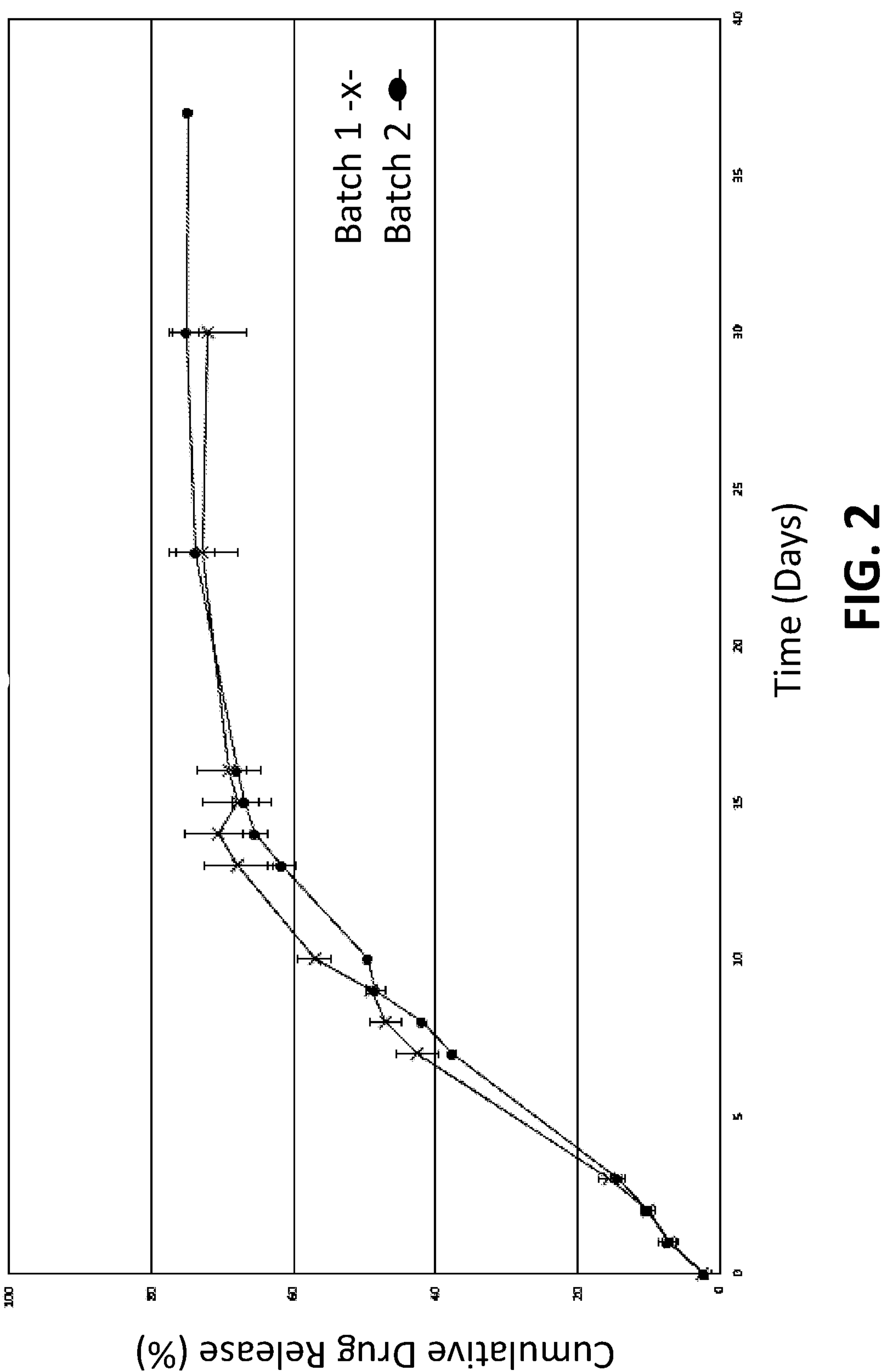
FIG. 2 is a graph showing in vitro release data for cumulative nalmefene release over time for two example nalmefene-containing polymer microsphere formulations.

Batch 1 was tested in an in vitro assay mimicking physiological conditions. The cumulative percent release of nalmefene over time is shown graphically in FIG. 2.

Example 3—Preparation of PLGA-Based Nalmefene-Encapsulated Polymer Microspheres Batch 2: Following the general procedure described in Example 1 and illustrated in FIG. 1, the DP was formed by dissolving 11.0 g of 85:15, acid terminated PLGA having IV=0.62 dL/g and MW=78.4 kDa in 99.5 g of EA and 18.0 g of DMSO (EA:DMSO (5.5:1)), followed by addition of nalmefene (9.0 g) with mixing until completely dissolved. The DP was filtered and pumped at a flow rate of 180 mL/min into a Levitronix® BPS-i100 integrated pump system operating at 2,500 RPM. The CP comprising 0.35% PVA was also pumped into the homogenizer at a flow rate of 0.54 L/min (CP:DP=3:1).

The formed or forming microspheres exited the homogenizer and entered the SRV. Room temperature deionized water was added to the SRV, followed by water washing (room temperature and 35-39° C.) and a hollow fiber filter.

The bulk suspension was collected via filtration and lyophilized to obtain a free-flowing powder with a yield of about 64%. The drug load was 43.4 wt/wt % (96% drug encapsulation efficiency based on a target drug load of 45 wt/wt %). The average particle size was 13 μm ($D_{10}$), 22 μm ($D_{50}$), 36 μm ($D_{90}$). Residual solvents were EA=0.3% and DMSO=0.7%. The sample molecular weight was 76 kDa.

Batch 2 was tested in an in vitro assay mimicking physiological conditions. The cumulative percent release of nalmefene over time is shown graphically in FIG. 2.

Figures 3A, 3B, 3C:
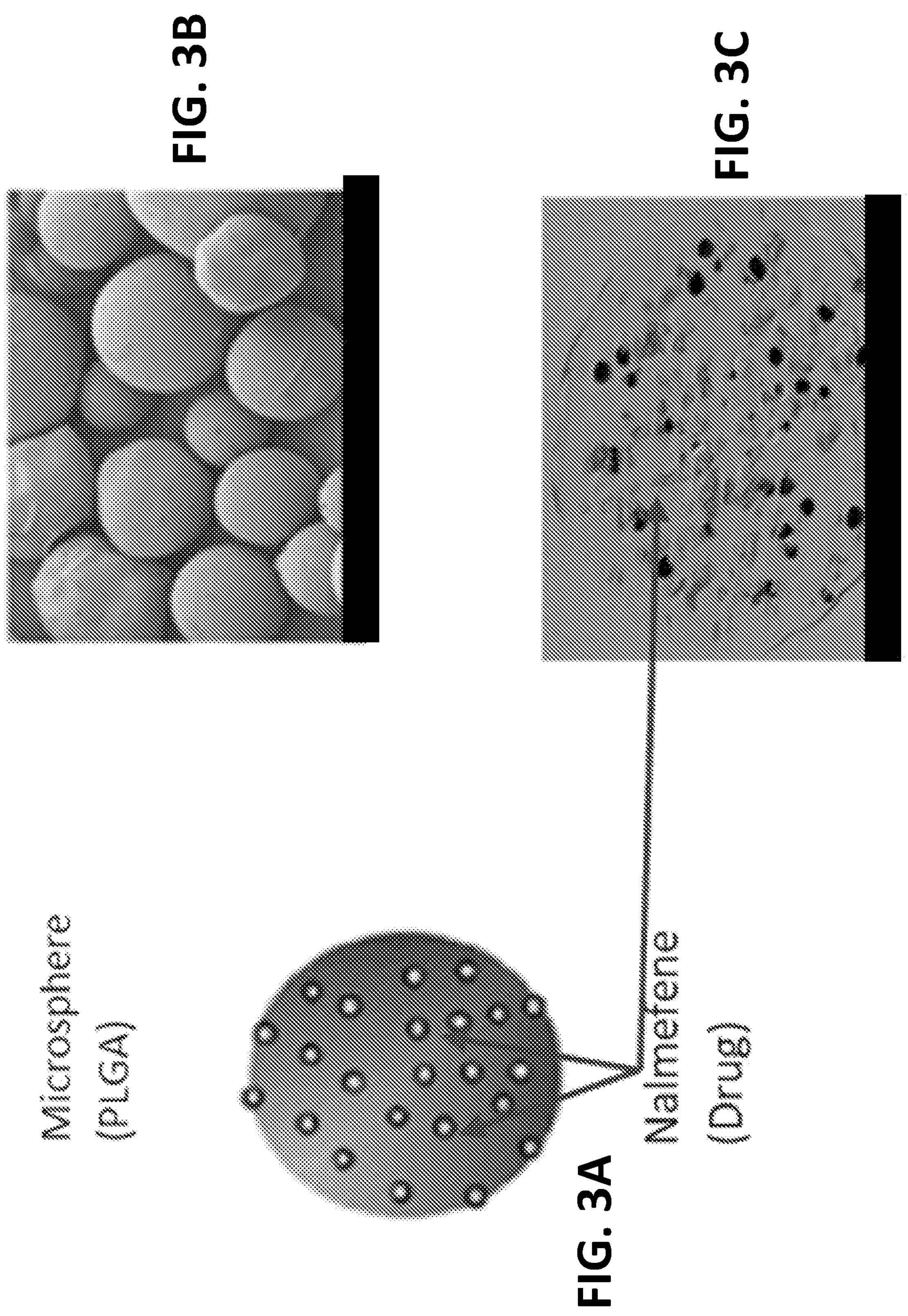
FIGS. 3A-3C depict example microspheres as described herein.

Example 4—Preparation and Testing of Long-Acting/Sustained Release Nalmefene Formulation Particles were formed by mixing two immiscible solvents (solvent 1 contains dissolved PLGA and Nalmefene, and solvent 2 is water containing a surfactant) at high speeds. This results in the formation of droplets containing acid end-capped PLGA (85:15; 50-80 kDa) and Nalmefene surrounded by the surfactant. Evaporation of solvent 1 from the droplet causes precipitation of the PLGA polymer resulting in the formation of a microparticle matrix enveloping or encapsulating the Nalmefene. Solvent 2 is removed by filtration or centrifugation, and the surfactant is then suitably washed off by water. The Nalmefene microparticles are dried further using a fluidized bed or a rotating oven to remove any residual water (water content<5%). The drug load was 25 wt/wt %. FIGS. 3A-3C depict the resulting microspheres.

The resulting nalmefene PLGA microparticles were injected into a rat model as described below to determine the duration and amount of nalmefene released (average plasma concentration of nalmefene) from the microparticles.

A small-animal formulation screening study was conducted using male Sprague-Dawley rats (Charles River Laboratories, Mattawan, MI) to determine the pharmacokinetic profile of the microparticles. Studies were performed by a single intramuscular (IM) injection of PLGA Nalmefene microparticles (suspended in diluent) or by a single IM injection of a control formulation into rats weighing 300-350 gram. The release of the drug was monitored over approximately three months by collecting blood samples at defined time points.

For dose preparation, vials containing freeze dried PLGA nalmefene microspheres were reconstituted with diluent (containing CMC-Na, Tween 80 and salt) and subsequently injected intramuscularly at the left hind limb at a target dose of 33.8 mg/kg Nalmefene and a dose volume of 0.5 mL/kg.

Blood samples of 0.3-0.5 ml were collected after drug administration at the sublingual vein using K2EDTA as an anticoagulant at the following time intervals (hours): 1, 3, 6, 12, 24 (Day 2), 48 (Day 3), 72 (Day 4), 120 (Day 6), 168 (Day 8), 336 (Day 15), 504 (Day 22), 672 (Day 29), 840 (Day 36), 1008 (Day 43), 1176 (Day 50), 1344 (Day 57), 1512 (Day 64), 1848 (Day 78), and 2136 (Day 90), for the test group; and 0.167, 0.333, 0.5, 1, 2, 4, 10, and 24 (Day 2) for the control group. After collection, the samples were centrifuged. The serum was collected and frozen before been analyzed using a validated analytical method.

Figure 4:
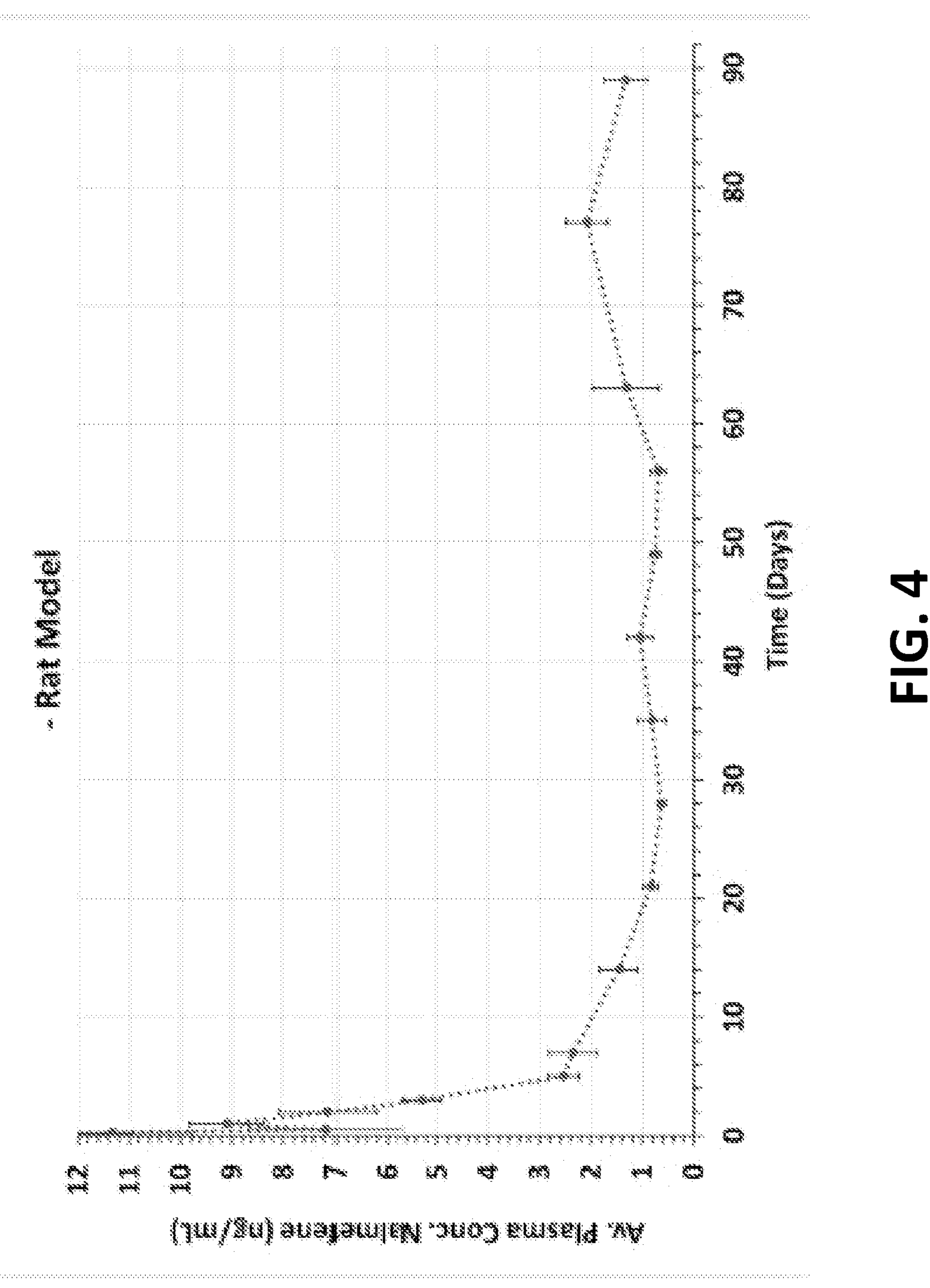
FIG. 4 shows the results of a pharmacokinetic study on rats using example microspheres as described herein.

A non-compartmental approach consistent with the IM route of administration employing validated WinNonlin 8.2 software (Trial vision, Pharsight Corp., USA) and MS Excel were used for parameter estimation. FIG. 4 shows the result of the rat study, illustrating an average plasma concentration of nalmefene of greater than about 0.87 ng/mL over a sustained period of about 90 days.

The aspects disclosed herein are not intended to be exhaustive or to be limiting. A skilled artisan would acknowledge that other aspects or modifications to instant aspects can be made without departing from the spirit or scope of the invention. The aspects of the present disclosure, as generally described herein and illustrated in the figures, can be arranged, substituted, combined, separated, and designed in a wide variety of different configurations, all of which are contemplated herein.

Unless otherwise specified, "a," "an," "the," "one or more of," and "at least one" are used interchangeably. The singular forms "a", "an," and "the" are inclusive of their plural forms. The recitations of numerical ranges by endpoints include all numbers subsumed within that range (e.g., 1 to 5 includes 1, 1.5, 2, 2.75, 3, 3.80, 4, 5, etc.). The terms "comprising" and "including" are intended to be equivalent and open-ended. The phrase "consisting essentially of" means that the composition or method may include additional ingredients and/or steps, but only if the additional ingredients and/or steps do not materially alter the basic and novel characteristics of the claimed composition or method. The phrase "selected from the group consisting of" is meant to include mixtures of the listed group.

When reference is made to the term "each," it is not meant to mean "each and every, without exception." For example, if reference is made to microsphere formulation comprising polymer microspheres, and "each polymer microsphere" is said to have a particular API content, if there are 10 polymer microspheres, and two or more of the polymer microspheres have the particular API content, then that subset of two or more polymer microspheres is intended to meet the limitation.

The term "about" in conjunction with a number is simply shorthand and is intended to include+10% of the number. This is true whether "about" is modifying a stand-alone number or modifying a number at either or both ends of a range of numbers. In other words, "about 10" means from 9 to 11. Likewise, "about 10 to about 20" contemplates 9 to 22 and 11 to 18. In the absence of the term "about," the exact number is intended. In other words, "10" means 10.

What is claimed is:

1. A microsphere formulation, comprising:

polymer microspheres, each polymer microsphere comprising:

(i) nalmefene; and (ii) a biodegradable polymer, wherein each polymer microsphere comprises a drug load of nalmefene of at least about 25% by weight of the polymer microsphere, and wherein the polymer microspheres have an average particle size of from about 10 μm to about 40 μm ($D_{50}$), and wherein the formulation releases the nalmefene at an amount of at least 0.5 ng/ml over a sustained period of at least 60 days.

2. The microsphere formulation of claim 1, wherein the nalmefene comprises a free base.

3. The microsphere formulation of claim 1, wherein the biodegradable polymer comprises an acid end-capped poly (D,L-lactide-co-glycolide) polymer.

4. The microsphere formulation of claim 1, wherein the biodegradable polymer comprises an acid end-capped, 85:15 poly (D,L-lactide-co-glycolide) polymer.

5. The microsphere formulation of claim 1, wherein the biodegradable polymer comprises an acid end-capped poly (D,L-lactide-co-glycolide) polymer having an inherent viscosity (IV) of between about 0.6 dL/g and 0.8 dL/g.

6. The microsphere formulation of claim 1, wherein the biodegradable polymer comprises an acid end-capped poly (D,L-lactide-co-glycolide) polymer having an IV of about 0.62 dL/g.

7. The microsphere formulation of claim 1, wherein each polymer microsphere has a nalmefene drug load of about 35 wt/wt % to about 45 wt/wt %.

8. The microsphere formulation of claim 1, wherein the polymer microspheres have an average particle size of between about 15 μm and about 30 μm ($D_{50}$).

9. The microsphere formulation of claim 1, characterized in that about 75% to 100% of the nalmefene is released over a period of within about 60 days of injection into a subject, but not more than about 20% of the nalmefene is released within about 24 hours of injection into the subject.

10. A microsphere formulation comprising polymer microspheres, each polymer microsphere comprising:

(i) nalmefene; and (ii) a biodegradable polymer comprising an acid end-capped poly (D,L-lactide-co-glycolide) polymer having an inherent viscosity (IV) of between about 0.6 dL/g and 0.8 dL/g, wherein each polymer microsphere comprises a drug load of greater than 25 wt/wt %, and wherein the polymer microspheres have an average particle size of between about 10 μm to about 40 μm ($D_{50}$), for use as a medicament for the treatment of alcohol and/or opioid dependence, wherein the formulation releases nalmefene at an amount of at least 0.5 ng/mL over a sustained period of at least 60 days.

11. The microsphere formulation of claim 10, wherein each polymer microsphere has a nalmefene drug load of about 40 wt/wt % to about 45 wt/wt %.

12. The microsphere formulation of claim 10, wherein the polymer microspheres have an average particle size of between about 15 μm and about 25 μm ($D_{50}$).

13. The microsphere formulation of claim 10, wherein the treatment comprises intramuscular or subcutaneous injection of the microsphere formulation to a patient in need thereof no more frequently than about every 60 days.

14. A nalmefene formulation, comprising:

a. a microsphere comprising poly(lactic-co-glycolic acid) (PLGA) with a ratio of lactide to glycolide of between 80:20 to 90:10; and b. a nalmefene base loaded into the microsphere at an amount of at least 20% w/w, relative to the microparticle, wherein the formulation releases nalmefene at an amount of at least 0.5 ng/ml over a sustained period of at least 80 days.

15. The nalmefene formulation of claim 14, wherein the ratio of lactide to glycolide is between 82:18 to 88:12.

16. The nalmefene formulation of claim 15, wherein the ratio of lactide to glycolide is about 85:15.

17. The nalmefene formulation of claim 14, wherein the nalmefene base is loaded in to the microsphere in an amount of at least 25% w/w, relative to the microsphere.

18. The nalmefene formulation of claim 14, wherein the formulation releases nalmefene at an amount of at least 1.3 ng/ml over a sustained period of at least 90 days.

19. The nalmefene formulation of claim 14, wherein the formulation releases nalmefene over a sustained period of 80 days to 100 days.

20. The nalmefene formulation of claim 14, wherein the PLGA has a molecular weight of between 50-80 kDa.

21. The nalmefene formulation of claim 14, wherein the PLGA comprises acid endcaps.

22. The nalmefene formulation of claim 14, wherein the microsphere has an average particle size of between about 60 μm to about 100 μm.

23. The nalmefene formulation of claim 14, wherein the nalmefene base has an average particle size of between about 2 μm to about 5 μm.

24. The nalmefene formulation of claim 14, wherein the formulation is lyophilized.

25. The nalmefene formulation of claim 14, further comprising a diluent including water, carboxymethylcellulose sodium, polysorbate 20, and sodium chloride.

26. A nalmefene formulation, comprising:

a. a microsphere comprising poly(lactic-co-glycolic acid) (PLGA) with a ratio of lactide to glycolide of between 82:18 to 88:12, a molecular weight of between 50-80 kDa, and an average particle size of between about 60 μm to about 100 μm; and b. a nalmefene base having an average particle size of about 2 μm to about 5 μm, loaded into the microsphere at an amount of at least 30% w/w, relative to the microsphere, wherein the formulation releases nalmefene at an amount of at least 1.0 ng/ml over a sustained period of at least 90 days.

27. The nalmefene formulation of claim 26, wherein the ratio of lactide to glycolide is about 85:15.

28. The nalmefene formulation of claim 26, wherein the formulation releases nalmefene at an amount of at least 1.3 ng/ml over a sustained period of 80 days to 100 days.

29. The nalmefene formulation of claim 26, wherein the PLGA comprises of acid end-caps.

30. The nalmefene formulation of claim 26, wherein the microsphere has an average particle size of between about 75 μm to about 85 μm.

31. The nalmefene formulation of claim 26, wherein the formulation is lyophilized.

32. The nalmefene formulation of claim 26, further comprising a diluent including water, carboxymethylcellulose sodium, polysorbate 20, and sodium chloride.

* * * * *